US00PP22252P2

(12) United States Plant Patent
Krassenburg

(10) Patent No.: US PP22,252 P2
(45) Date of Patent: Nov. 15, 2011

(54) ***IMPATIENS* PLANT NAMED 'SILT ORAGSAR'**

(50) Latin Name: *Impatiens walleriana*
Varietal Denomination: Silt Oragsar

(75) Inventor: Jolanda Krassenburg, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/803,159

(22) Filed: Jun. 21, 2010

(51) Int. Cl.
*A01H 5/00* (2006.01)

(52) U.S. Cl. ..... Plt./317

(58) Field of Classification Search ..... Plt./317
See application file for complete search history.

*Primary Examiner* — Susan McCormick Ewoldt
(74) *Attorney, Agent, or Firm* — S. Matthew Edwards

(57) ABSTRACT

A new *Impatiens* plant named 'Silt Oragsar' particularly distinguished by the fully-double orange-red and white bi-colored flowers, has early flowering, nicely contrasting dark green foliage, and compact and low mounding plant habit with good branching.

1 Drawing Sheet

Latin name of the genus and species of the plant claimed: *Impatiens walleriana.*

Varietal denomination: 'Silt Oragsar'.

BACKGROUND OF THE NEW PLANT

The present invention comprises a new *Impatiens*, botanically known as *Impatiens walleriana*, and hereinafter referred to by the variety name 'Silt Oragsar'.

'Silt Oragsar' is a product of a planned breeding program. The new cultivar has fully-double orange-red and white bi-colored flowers, has early flowering, nicely contrasting dark green foliage, and compact and low mounding plant habit with good branching.

'Silt Oragsar' originated from a hybridization made in April 2007 in a controlled breeding environment in Andijk, Netherlands. The female parent was the unpatented, proprietary plant designated 'IDO3-27-11', with scarlet and white bi-colored flowers.

The male parent of 'Silt Oragsar' was an unpatented proprietary plant designated as 'IDO3-30-11', with salmon and white bi-colored flowers. The resultant seed was sown in June 2007.

'Silt Oragsar' was selected as one flowering plant within the progeny of the stated cross in the September 2007 in a controlled environment in Andijk, Netherlands.

The first act of asexual reproduction of 'Silt Oragsar' was accomplished when vegetative cuttings were propagated from the initial selection in September 2007 in a controlled environment in Andijk, Netherlands.

BRIEF SUMMARY OF INVENTION

Horticultural examination of plants grown from cuttings of the plant initiated in September 2007, and continuing thereafter, has demonstrated that the combination of characteristics as herein disclosed for 'Silt Oragsar' are firmly fixed and are retained through successive generations of asexual reproduction.

'Silt Oragsar' has not been observed under all possible environmental conditions. The phenotype may vary significantly with variations in environment such as temperature, light intensity and day length.

Plant Breeder's Rights for this cultivar were applied for in Canada on Feb. 18, 2010 (#10-6848), in CPVO on Mar. 18, 2010 (#2010/0685), and in Switzerland on Oct. 29, 2009 (#309-2620). 'Silt Oragsar' has not been made publicly available more than one year prior to the filing of this application.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

The accompanying photographic drawing shows typical flower and foliage characteristics of 'Silt Oragsar' with colors being as true as possible with an illustration of this type. The photographic drawing shows a flowering potted plant of the new variety growing in a 4 inch pot, and a close-up of the flowers.

DETAILED BOTANICAL DESCRIPTION

The aforementioned photographs were taken in Gilroy, Calif. from plants growing in a greenhouse trial in April 2010. These plants were approximately 9-10 weeks of age. The plant descriptions and measurements were taken on those very same plants later in early June 2010 after growing outdoors a few weeks in a 8 inch pot. They were about 16 weeks of age.

Color references are made to The Royal Horticultural Society Colour Chart (R.H.S.) 2001.

TABLE 1

DIFFERENCES BETWEEN THE NEW VARIETY 'SILT ORAGSAR' AND A SIMILAR VARIETY

| | 'Silt Oragsar' | Silte Oransar' (U.S. Plant Pat. No. 18,029) |
|---|---|---|
| Flower color: | More orange-red | More red-orange |
| Foliage color: | Darker | Lighter |
| Branching habit: | More | Fewer |

Plant:
*Form, growth and habit.*—Compact, low mounded, good branching.
*Plant height.*—21-24 cm.
*Plant height (inflorescence included).*—23-26 cm.
*Plant width.*—50-55 cm.
Roots:
*Number of days to initiate roots.*—4 days at about 22 degrees C.
*Number of days to produce a rooted cutting.*—4-8 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—Closest to RHS 147A.
*Lower surface.*—RHS 147B to RHS 147C with blotches of about RHS 176B.
*Mature, leaf color, upper surface.*—Closest to RHS 147A.
*Lower surface.*—RHS 147B to RHS 147C with blotches of about RHS 176B.
*Length.*—6.3-7.5 cm.
*Width.*—3.3-4.5 cm.
*Shape.*—Elliptical to ovate.
*Base shape.*—Attenuate.
*Apex shape.*—Acute.
*Margin.*—Crenate; toothed.
*Texture, upper surface.*—Glabrous.
*Lower surface.*—Glabrous.
*Color of veins, upper surface.*—RHS 155C basally to indistinct within the blade.
*Color of veins, lower surface.*—RHS 155C basally turning to about RHS N199A.
*Petiole color.*—RHS 155B with slight anthocyanin spots of about RHS 166B.
*Length.*—0.6-1.5 cm.
*Diameter.*—0.25-0.4 cm.
*Texture.*—Glabrous.
Stem:
*Color of stem.*—RHS 145C with anthocyanin spots of about RHS 176C.
*Length of stem.*—16-20 cm.
*Diameter.*—0.5-0.7 cm.
*Length of internodes.*—2.0-4.0 cm.
*Texture.*—Glabrous.
*Color of peduncle.*—RHS 144C but more translucent.
*Length of peduncle.*—1.2 cm.
*Peduncle diameter.*—0.1 cm.
*Texture.*—Glabrous.
Inflorescence:
*Type.*—Appear from the upper leaf nodes of the stem, usually a peduncle bears two flowers.
*Blooming habit.*—Continuous flowering throughout the season.
*Quantity of flowers per plant.*—120-150 plus buds.
*Lastingness of individual blooms on the plant.*—5-8 days.
*Fragrance.*—None.
Bud (just when showing color):
*Color.*—RHS N30A and RHS N155B but whiter.
*Length.*—1.0-1.2 cm.
*Width.*—0.7-0.8 cm.
*Shape.*—Oval.
Immature inflorescence:
*Diameter.*—About 3.5-3.9 cm.
*Color of petals, upper surface.*—RHS N30A and RHS N155B but whiter.
*Lower surface.*—RHS 40B and RHS N155B but whiter.
Mature inflorescence:
*Diameter.*—4.4-4.7 cm.
*Depth.*—1.5-1.7 cm.
*Color of petals, upper surface.*—RHS N30A but slightly lighter and RHS N155B but whiter.
*Lower surface.*—RHS N155b but whiter with RHS 40b to RHS 40C wide band on the margins.
*Length.*—2.2-2.4 cm.
*Width.*—1.5-1.8 cm.
*Shape.*—Obovate.
*Apex shape.*—Rounded.
*Margin.*—Entire.
*Texture, upper surface.*—Papillose.
*Lower surface.*—Papillose.
Calyx:
*Quantity of sepals.*—5; 2 larger, one a modified spur and 2 smaller.
*Larger sepals.*—
*Color, upper surface.*—RHS 145C.
*Lower surface.*—RHS 145C with RHS 145C margins and RHS 143B keel.
*Length.*—About 1.5 cm.
*Width.*—1.0 cm.
*Shape.*—Broadly elliptical.
*Apex shape.*—Mucronulate.
*Based.*—Fused.
*Margins.*—Entire.
*Texture, upper surface.*—Papillose.
*Lower surface.*—Papillose.
Smaller sepals:
*Color, upper surface.*—RHS 137C.
*Lower surface.*—RHS 137C.
*Length.*—0.3 cm.
*Width.*—0.1 cm.
*Shape.*—Lanceolate.
*Apex shape.*—Acute.
*Based.*—Fused.
*Margins.*—Entire.
*Texture, upper surface.*—Glabrous.
*Lower surface.*—Glabrous.
*Spur, color.*—RHS 145D basally with anthocyanins of about RHS 178C and RHS 178B at the tip.
*Length.*—2.2-3.0 cm.
*Diameter.*—0.15 cm at the midpoint.
Reproductive organs: Usually none, only occasionally in rudimental form, as all stamen are transformed into petals
Fertility/seed set: Fertility/seed set has not been observed on this hybrid.
Disease/pest resistance: Disease/pest resistance has not been observed on this hybrid.

What is claimed is:

1. A new and distinct variety of *Impatiens* plant named 'Silt Oragsar' substantially as illustrated and described herein.

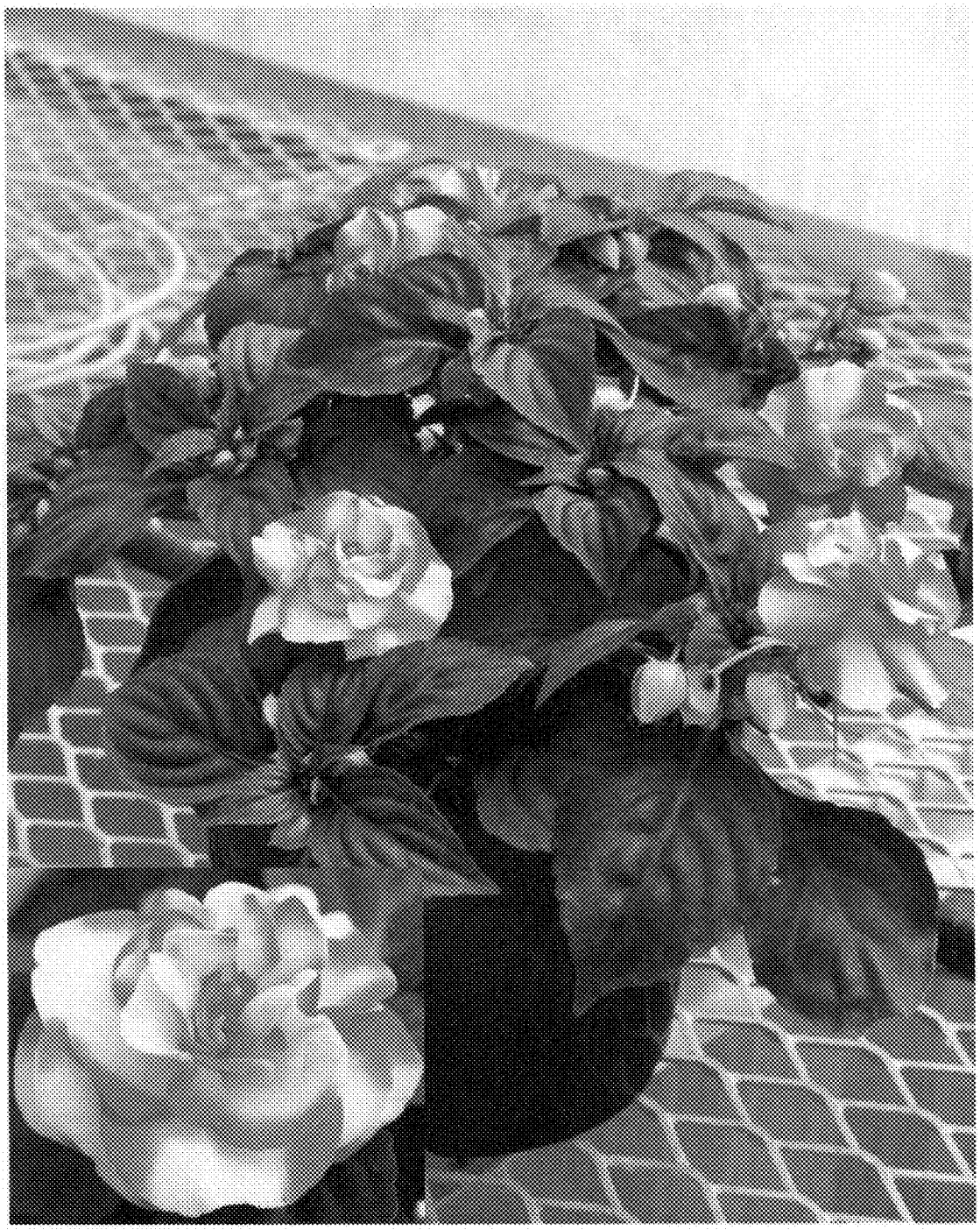

* * * * *